(12) United States Patent
Ko et al.

(10) Patent No.: US 9,303,022 B2
(45) Date of Patent: Apr. 5, 2016

(54) INDUSTRIAL METHOD FOR THE PREPARATION OF HIGH-PURITY METHIOZOLIN

(71) Applicants: Moghu Research Center Ltd., Daejeon (KR); Korea Research Institute of Chemical Technology, Daejeon (KR)

(72) Inventors: Young Kwan Ko, Daejeon (KR); Dong Wan Koo, Daejeon (KR); Jae Chun Woo, Daejeon (KR); Jae Wook Ryu, Daejeon (KR); Suk Jin Koo, Daejeon (KR); Ki Hwan Hwang, Daejeon (KR); Dong Guk Lee, Daejeon (KR); Kun Hoe Chung, Daejeon (KR); Man Seok Jeon, Daejeon (KR); Sung Hun Kim, Daejeon (KR); Jong Su Lim, Daejeon (KR); Nam Gyu Cho, Daejeon (KR)

(73) Assignees: MOGHU RESEARCH CENTER LTD., Daejeon (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 14/398,114

(22) PCT Filed: Mar. 18, 2013

(86) PCT No.: PCT/KR2013/002160
§ 371 (c)(1),
(2) Date: Oct. 30, 2014

(87) PCT Pub. No.: WO2013/151250
PCT Pub. Date: Oct. 10, 2013

(65) Prior Publication Data
US 2015/0158852 A1 Jun. 11, 2015

(30) Foreign Application Priority Data

Apr. 2, 2012 (KR) ........................ 10-2012-0033835

(51) Int. Cl.
*C07D 413/04* (2006.01)
*B01J 31/02* (2006.01)

(52) U.S. Cl.
CPC ........... *C07D 413/04* (2013.01); *B01J 31/0271* (2013.01)

(58) Field of Classification Search
None
See application file for complete search history.

(56) References Cited

U.S. PATENT DOCUMENTS 6,838,416 B2  1/2005  Ryu et al.
7,998,902 B2  8/2011  Koo et al.

OTHER PUBLICATIONS

Nam, J.H. et al. Synthesis and Herbicidal Activities of Enantiopure Methiozolines. Bulletin of the Korean Chemical Society, Jan. 20, 2012. vol. 33, No. 1, pp. 297-300.
Hwang, I.T. et al. Journal of Agricultural and Food Chemistry. 2005. vol. 53, pp. 8639-8643.

*Primary Examiner* — Kamal Saeed
(74) *Attorney, Agent, or Firm* — The PL Law Group, PLLC

(57) ABSTRACT

Provided is an industrial method for the preparation of [5-{(2,6-difluorobenzyloxy)methyl}-4,5-dihydro-5-methyl-3-(3-methylthiophene-2-yl)-isoxazole](common name: methiozolin) represented by Formula 1 that is a herbicidal substance in high-purity.

8 Claims, No Drawings

INDUSTRIAL METHOD FOR THE PREPARATION OF HIGH-PURITY METHIOZOLIN

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/002160, filed Mar. 18, 2013, which claims priority to Korean Patent Application No. 10-2012-0033835, filed Apr. 2, 2012, entire contents of which are incorporated herein by reference.

TECHNICAL FIELD

The present invention relates to an industrial method for the preparation of [5-{(2,6-difluorobenzyloxy)methyl}-4,5-dihydro-5-methyl-3-(3-methylthiophene-2-yl)-isoxazole] (common name: methiozolin) represented by Formula 1 that is a herbicidal substance, and in particular, to an industrial method for the preparation of high-purity methiozolin in which according to Reaction Scheme 1,4,5-dihydro-5-methyl-3-{(3-methylthiophene-2-yl)-isoxazole-5-yl}methanol (Formula 2) is reacted with 2,6-difluorobenzyl chloride (or bromide)(Formula 3) in the presence of an alkali metal salt and a phase transfer catalyst in a water-organic solvent system at a temperature of 50 to 100° C. to provide an organic layer concentrate, which is then subjected to a purification process employing crystallization to afford high-purity methiozolin.

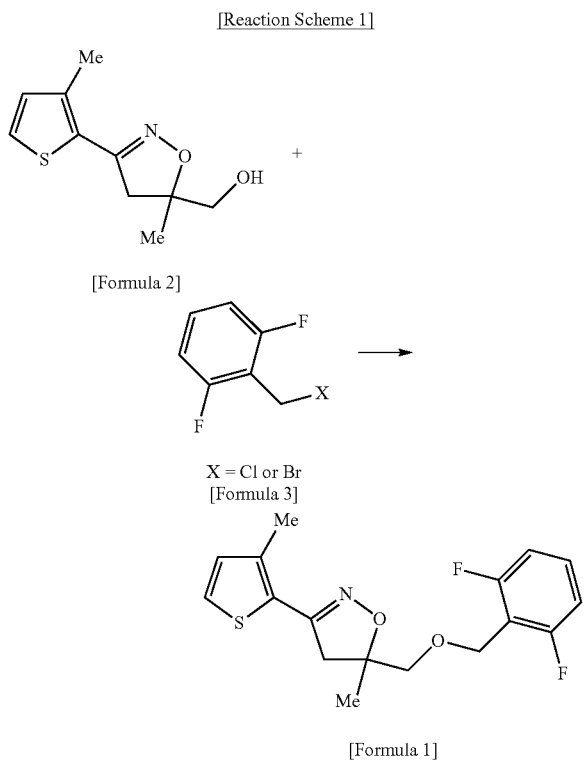

[Reaction Scheme 1]

[Formula 2]

X = Cl or Br
[Formula 3]

[Formula 1]

BACKGROUND ART

Regarding a herbicidal compound having the chemical structure of thiopheneisoxazoline, U.S. Pat. No. 6,838,416 B2 discloses a thiopheneisoxazoline compound represented by Formula 4 below.

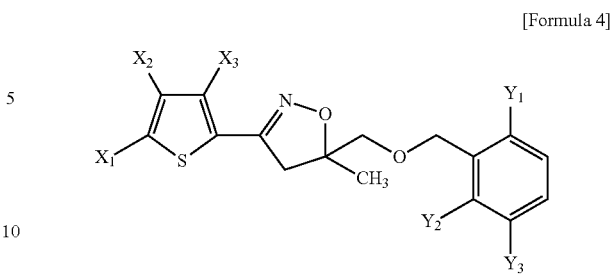

[Formula 4]

(wherein, $X_1$, $X_2$, and $X_3$ represent each a hydrogen atom, an alkyl group, a halogen group, a methoxy group, or a nitro group, and $Y_1$, $Y_2$, and $Y_3$ represent each a hydrogen atom or a fluorine atom).

This patent document discloses that in the synthetic procedure of thiopheneisoxazoline derivatives including the compound of Formula 1, coupling reaction is performed using sodium hydride as a base in an anhydrous condition. However, this method is appropriate only for small-scale synthesis in a laboratory, and is not appropriate for industrial large-scale production.

A prior art [*J. Agric. Food Chem.* 2005, 53, 8639-8643] describes the method for the preparation of methiozolin based on this patent in detail. The prior art discloses that according to Reaction Scheme 1, 4,5-dihydro-5-methyl-3-{(3-methylthiophene-2-yl)-isoxazole-5-yl}methanol (Formula 2) and 2,6-difluorobenzylbromide (Formula 3) are reacted employing sodium hydride as a base in a DMF solvent at a temperature of 60 to 70° C., and after completion of the reaction the reaction mixture is diluted with an organic solvent, washed with water and the resulting organic layer is concentrated, and then subjected to column chromatography to perform pre-purification, and then, the obtained pre-purified product is crystallized in n-hexane to obtain a target material in the yield of about 60%. However, this method is applicable only to small-scale laboratorial synthesis because an anhydrous condition is required to use sodium hydride as a base, and after reaction, column chromatography must be performed as a pre-purification procedure to remove mineral oil contained in sodium hydride, and is not appropriate for industrial synthesis for mass production.

Another prior art [Bull. Korean Chem. Soc. 2012, Vol. 33, No. 1, 297-300] describes a method of producing (R)-methiozolin (Formula 1a) or (S)-methiozolin (Formula 1 b) that is a methiozolin stereoisomer, in which according to Reaction Scheme 2 and Reaction Scheme 3, (R) or (S) 4,5-dihydro-5-methyl-3-{(3-methylthiophene-2-yl)-isoxazole-5-yl}methanol (Formula 2a or Formula 2b) and 2,6-difluorobenzylchloride (Formula 3) are reacted employing sodium hydroxide as a base in THF solvent at a temperature of 60-70° C., and after completion of the reaction the reaction mixture is diluted with an organic solvent, washed with water and the resulting organic layer is concentrated, and then subjected to column chromatography to perform pre-purification, and the pre-purified product is crystallized in n-hexane to obtain a target material in the yield of about 60%. In this case, the yield is also low, and due to the pre-purification procedure employing column chromatography, this method is not appropriate for industrial synthesis for mass production.

[Reaction Scheme 2]

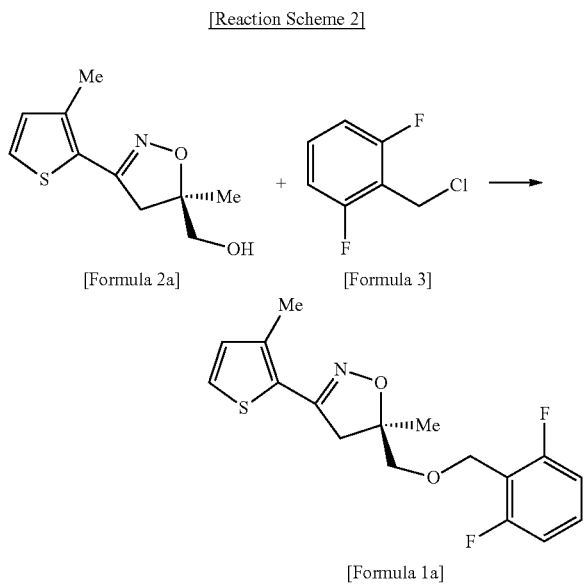

[Formula 2a]    [Formula 3]

[Formula 1a]

[Reaction Scheme 3]

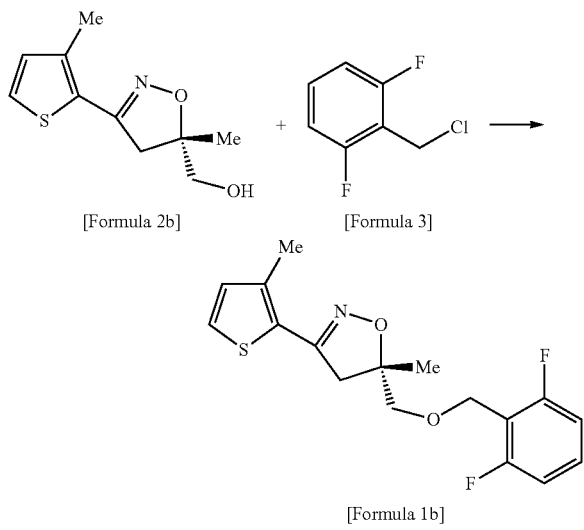

[Formula 2b]    [Formula 3]

[Formula 1b]

U.S. Pat. No. 6,838,416 B2 discloses that methiozolin of Formula 1 is suitable for a paddy rice herbicide, and U.S. Pat. No. 7,998,902 discloses that methiozolin is suitable for a turf herbicide. However, when impurities other than methiozolin are included in the manufacturing process for commercialization of methiozolin, the impurities included may cause toxicity or environmental problems. Accordingly, when produced in great quantities, methiozolin, which is a target material, needs to be produced in as high purity as possible.

As described above, to commercialize methiozolin of Formula 1 as herbicide, there is a need to develop an industrial process that is applicable for mass production of high-purity methiozoline in high yield.

SUMMARY

The present invention provides an industrial method for the preparation of high-purity methiozolin to commercialize methiozolin that is the compound of Formula 1.

The inventors of the present invention made efforts to develop a novel industrial method for the preparation of high-purity methiozolin that is the compound represented by Formula 1 in high-yield, and as a result, found a reaction condition that when 4,5-dihydro-5-methyl-3-{(3-methylthiophene-2-yl)-isoxazole-5-yl}methanol (the compound of Formula 2) is reacted with 2,6-difluorobenzylchloride (or bromide) (the compound of Formula 3) in the presence of an alkali metal salt and a phase transfer catalyst in a mixed solvent system including water and an organic solvent, the formation of by-products can be minimized, and also found a method for the purification of the crude product employing crystallization without the use of column chromatography.

As explained and confirmed above, according to the present invention, high-purity methiozolin with high turf/crop selectivity and herbicidal activity can be produced in high-yield. Productivity during cultivation of crop and management of turf may be substantially improved. Also, highly-added values are created, leading to high economic effects.

DETAILED DESCRIPTION

The present invention provides a method for the preparation of methiozolin represented by Formula 1 in high yield in which according to Reaction Scheme 1, 4,5-dihydro-5-methyl-3-{(3-methylthiophene-2-yl)-isoxazole-5-yl}methanol represented by Formula 2 is reacted with 2,6-difluorobenzylchloride (or bromide) represented by Formula 3 in the presence of an alkali metal salt and a phase transfer catalyst in a mixed solvent system including water and an organic solvent at a temperature of 50 to 100° C. In detail, the present invention provides a method for the preparation of methiozolin represented by Formula 1 in high yield in which 4,5-dihydro-5-methyl-3-{(3-methylthiophene-2-yl)-isoxazole-5-yl}methanol represented by Formula 2 is reacted with 2,6-difluorobenzyl(chloride or bromide) represented by Formula 3 in the presence of an alkali metal salt and a phase transfer catalyst in the mixed solvent system including water and an organic at a temperature of 50 to 100° C., and a concentrate of an isolated organic layer is crystallized in a mixed solvent including water and alcohol or a mixed solvent including alcohol and aliphatic hydrocarbon.

The present invention will be described in detail.

The present invention provides an economic process for the preparation of high-purity methiozolin, in which the compound of Formula 2 is reacted with the compound of Formula 3 in the presence of optimized base and catalyst in a mixed solvent system including water and an organic solvent at a predetermined reaction temperature, and the resulting organic concentrate is crystallized through a selected solvent system.

In synthesizing the high-purity methiozolin represented by Formula 1 in high-yield, a reaction solvent system, a base, and a catalyst, and a reaction temperature are critical factors. Accordingly, in the present invention, these factors are optimized to minimize the formation of by-product of Formula 5 illustrated below, which is produced during reaction, and to effectively remove the by-product during purification procedure to produce the high-purity methiozolin in high-yield.

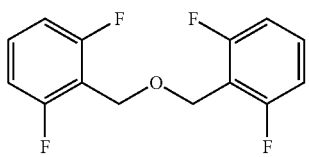

[Formula 5]

The compound of Formula 2 used herein as a starting material is a known compound disclosed in U.S. Pat. No. 6,838,416 B2, and may be synthesized and purified by using any known method. The compound of Formula 3 is a commercially available compound.

The compound of Formula 3 may be used in an amount of 1.0 to 1.2 eq. with respect to the compound of Formula 2.

The reaction is performed in a mixed solvent system including water and an organic solvent. The organic solvent may be benzene, toluene, xylene, chlorobenzene, or 1,2-dichloroethane. For example, the organic solvent may be toluene or 1,2-dichloroethane, and a volumetric ratio of water to the organic solvent may be in a range of 2:8 to 8:2.

The base used for reaction may be an alkali metal salt. For example, the base may be lithium hydroxide, sodium hydroxide, or potassium hydroxide. An amount of the base may be in a range of 4.0 to 6.0 eq. with respect to compound of Formula 2.

A phase transfer catalyst may be an ammonium salt or phosphonium salt. For example, the phase transfer catalyst as an ammonium salt may be tetrabutylammoniumhydrogensulfate, tetrabutylammoniumiodide, tetraethylammoniumbromide, tetraethylammoniumchloride, tetrabutylammoniumbromide, tetrabutylammoniumchloride, or benzyltriethylammoniumbromide. The phase transfer catalyst as a phosphonium salt may be tetraethylphosphoniumbromide, tetrabutylphosphoniumbromide, or tetrabutylphosphoniumchloride, but is not limited thereto, and may be used in an amount of 0.01 to 0.2 eq., for example, 0.01 to 0.1 eq.

The reaction temperature may be in a range of 50 to 100° C. However, in consideration of yield and purity, the reaction temperature may be in a range of 55 to 80° C., and for example, 60 to 65° C.

After completion of the reaction, the reaction mixture was cooled, and an isolated organic layer was dried and concentrated to provide a concentrate. The concentrate is purified by crystallization in a mixed solvent system of water/$C_1$ to $C_4$ alcohol or $C_1$ to $C_4$ alcohol/$C_5$ to $C_7$ aliphatic hydrocarbon. By doing so, high-purity methiozolin may be obtained in high yield in a simple and economic manner.

A $C_1$ to $C_4$ alcohol solvent used for crystallization in the water/$C_1$ to $C_4$ alcohol solvent system may be methanol, ethanol, propanol, isopropanol, or n-butanol, and a volumetric ratio of water to $C_1$ to $C_4$ alcohol may be in a range of 1:3 to 1:10, and a weight of water may be 4 to 6 times greater than that of the compound 2.

A hydrocarbon used for crystallization in a mixed solvent system of the $C_1$ to $C_4$ alcohol/$C_5$ to $C_7$ aliphatic hydrocarbon may be n-pentane, n-hexane, or n-heptane, and a $C_1$ to $C_4$ alcohol solvent may be methanol, ethanol, n-propanol, isopropanol, or n-butanol, and the volumetric ratio of the $C_1$ to $C_4$ alcohol to the $C_5$ to $C_7$ aliphatic hydrocarbon may be in a range of 1:5 to 1:50, and a weight of the alcohol used herein may be 0.2 to 1 times greater than that of the compound 2.

A crystallization temperature may be in a range of −20° C. to 20° C., for example, −10° C. to 10° C.

The purity of methiozolin synthesized herein may be 99% or more, for example, 99.0 to 99.9%, but is not limited thereto.

The present invention described above will be described in detail in the following examples. However, the present invention is not limited to the examples.

Example 1

Synthesis of Methiozolin

Toluene (18 L), 4,5-dihydro-5-methyl-3-{(3-methylthiophene-2-yl)-isoxazole-5-yl}methanol (25 kg, 118 mol), tetrabutylphosphoniumbromide (1.0 kg), and 25% NaOH solution (95 kg, 593 mol) were added to a 250 L stainless reactor, and the mixture was stirred. A solution of 2,6-difluorobenzylchloride (21 kg, 129 mol) dissolved in toluene (50 L) was added to the reaction mixture, and the resultant was heated at a temperature of 55 to 60° C. for 6 hours and then cooled to room temperature, and an organic layer was isolated. Activated carbon (2 kg) was added to the isolated brown organic layer and then the reaction mixture was stirred for about 0.5 hr, and filtered to remove the activated carbon. The residual solution was loaded into a 250 L reactor, and distillation was performed under reduced pressure at a temperature of 60° C. to remove toluene, and isopropanol (120 L) was added to the residue which was completely dissolved at a temperature of about 50° C. The isopropanol solution prepared above was cooled to 0° C., and then slowly added to a solution of isopropanol/water (240 L/120 L) which was well stirred at a temperature of 0° C. in a 630 L reactor to give a solid. After completion of addition, the resultant was placed at a temperature of 0° C. for about 1 hour, and then filtered. The solid was washed with n-hexane (20 L), and vacuum dried at a temperature of 30° C. for 12 hours to afford 30 kg (yield: 75%, purity: 99.7%) of methiozolin in the form of white solid (mp: 50 to 52° C.).

Example 2

Synthesis of Methiozolin

Toluene (73 L), 4,5-dihydro-5-methyl-3-{(3-methyl thiophene-2-yl)-isoxazole-5-yl}methanol (100 kg, 473 mol), tetrabutylphosphonium bromide (5.1 kg), and 25% NaOH solution (379 kg, 2,368 mol) were loaded into a 1,000 L stainless reactor and the mixture was stirred. A solution of 2,6-difluorobenzylchloride (84.6 kg, 520 mol) dissolved in toluene (200 L) was added to above reaction mixture, and the resultant was stirred at a temperature of 60 to 65° C. for 20 hours, and then cooled to room temperature, and an organic layer was isolated. The isolated organic layer was washed twice with water (194 L×2), and then distilled under reduced pressure at a temperature of 90° C. to remove toluene. Then, isopropanol (47 L) and n-heptane (473 L) were added to the residue which was completely dissolved by heating at a temperature of 60 to 70° C.

The resulting solution was cooled at a temperature of 0° C. and placed for 12 hours at that temperature to give solid product which was filtered, washed with n-hexane (95 L), and vacuum dried at a temperature of 30° C. for 6 hours to afford 148 kg (yield: 92%, purity: 99.5%) of methiozolin in the form of white solid (mp: 50 to 52° C.).

The yield and purity values of methiozolin according to reaction conditions and crystallization conditions used to perform synthesis processes according to Examples 1 and 2 are shown in Table 1 below.

TABLE 1

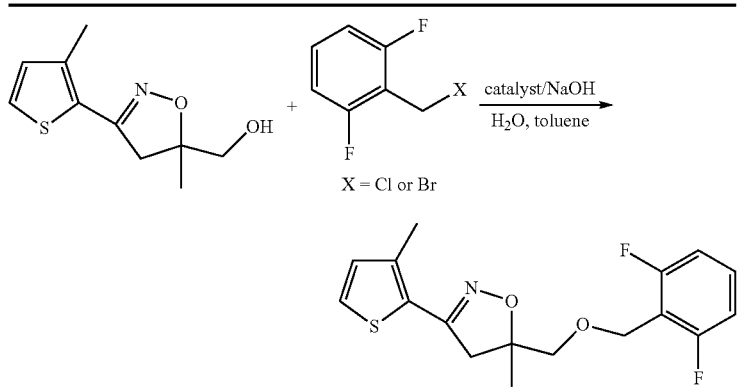

Optimization of methiozolin synthesis

| Entry | reaction temperature (° C.) | reaction time (hr) | X | catalyst (5%) | crystallization condition | yield[a] (purity[b]), % |
|---|---|---|---|---|---|---|
| 1 | 55-60 | 6 | Br | — | — | <5[c] |
| 2 | 55-60 | 6 | Cl | TBAH | H$_2$O/IPA (1:3) | 75 (99.7) |
| 3 | 55-60 | 6 | Br | TBAH | H$_2$O/EtOH (1:4) | 91 (99.0) |
| 4 | 55-60 | 20 | Cl | TBPB | H$_2$O/IPA (1:3) | 75 (99.7) |
| 5 | 60-65 | 20 | Cl | TBPB | H$_2$O/MeOH (1:3) | 75 (99.5) |
| 6 | 60-65 | 20 | Cl | TBPB | H$_2$O/EtOH (1:3) | 82 (98.0) |
| 7 | 60-65 | 20 | Cl | TBPB | H$_2$O/IPA (1:5) | 85 (99.0) |
| 8 | 60-65 | 20 | Cl | TBPB | MeOH/n-Hep (1:10) | 82 (99.5) |
| 9 | 60-65 | 20 | Cl | TBPB | EtOH/n-Hep (1:10) | 87 (99.5) |
| 10 | 60-65 | 20 | Cl | TBPB | IPA/n-Hep (1:10) | 92 (99.5) |

[a] yield of isolated material,
[b] HPLC purity,
[c] HPLC conversion yield, TBAH: (Bu)$_4$NHSO$_4$, TBPB: (Bu)4PBr, IPA: isopropyl alcohol, N-Hep: n-heptane One of ordinary skill in the art may easily synthesize high-purity methiozolin by using or applying the exemplary synthesis methods described above.

The invention claimed is:

1. A method for the preparation of high-purity methiozolin (Formula 1), the method comprising reaction of 4,5-dihydro-5-methyl-3-{(3-methylthiophene-2-yl)-isoxazole-5-yl}methanol represented by Formula 2 below with 2,6-difluorobenzyl chloride (or bromide) represented by Formula 3 below in the presence of an alkali metal salt and a phase transfer catalyst in a mixed solvent system comprising water and an organic solvent at a temperature of 50 to 100° C., followed by crystallizing a concentrate of an isolated organic layer in a mixed solvent comprising water and alcohol or a mixed solvent comprising alcohol and aliphatic hydrocarbon:

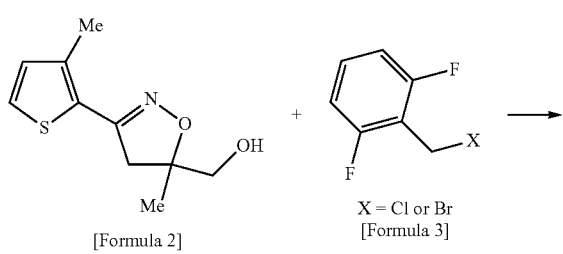

[Formula 2]     [Formula 3]

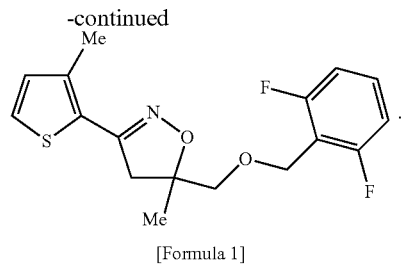

[Formula 1]

2. The method of claim 1, wherein the organic solvent is selected from the group consisting of benzene, toluene, xylene, chlorobenzene, and 1,2-dichloroethane.

3. The method of claim 1, wherein the alkali metal salt is selected from the group consisting of sodium hydroxide, potassium hydroxide, and lithium hydroxide.

4. The method of claim 1, wherein the phase transfer catalyst is selected from the group consisting of tetrabutylammoniumhydrogensulfate, tetrabutylammoniumbromide, and tetrabutylphosphoniumbromide.

5. The method of claim 1, wherein the mixed solvent used to purify methiozolin by crystallization of the concentrate of the isolated organic layer is a mixed solvent comprising water and a C$_1$ to C$_4$ alcohol or a mixed solvent comprising a C$_1$ to C$_4$ alcohol and a C$_5$ to C$_7$ aliphatic hydrocarbon.

6. The method of claim 5, wherein the mixed solvent used to purify methiozolin by crystallization of the concentrate of the isolated organic layer is a mixed solvent comprising water and isopropanol or a mixed solvent comprising isopropanol and n-heptane.

7. The method of claim 1, wherein toluene is used as the organic solvent of the mixed solvent system comprising water and the organic solvent, sodium hydroxide is used as the base, tetrabutylphosphoniumbromide is used as the phase transfer catalyst, a reaction temperature is in a range of 60 to 65° C., and the concentrate of the organic layer is crystallized in a mixed solvent comprising isopropanol and n-heptane.

8. The method of claim 1, wherein the high-purity indicates a purity of 99% or more.

\* \* \* \* \*